(12) United States Patent
Fang et al.

(10) Patent No.: US 12,413,866 B2
(45) Date of Patent: Sep. 9, 2025

(54) SYSTEM AND METHOD FOR VARIABLE ILLUMINATION INTELLIGENT IMAGING OF BILLION PIXEL LIGHT FIELD

(71) Applicant: TSINGHUA UNIVERSITY, Beijing (CN)

(72) Inventors: Lu Fang, Beijing (CN); Tao Yu, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 148 days.

(21) Appl. No.: 18/466,117

(22) Filed: Sep. 13, 2023

(65) Prior Publication Data

US 2024/0422446 A1  Dec. 19, 2024

(30) Foreign Application Priority Data

Jun. 19, 2023 (CN) .......................... 202310721980.3

(51) Int. Cl.
| | |
|---|---|
| *H04N 23/957* | (2023.01) |
| *A61B 5/11* | (2006.01) |
| *H04N 23/56* | (2023.01) |
| *H04N 23/611* | (2023.01) |
| *H04N 23/74* | (2023.01) |
| *H04N 23/90* | (2023.01) |

(52) U.S. Cl.
CPC ........... *H04N 23/957* (2023.01); *H04N 23/56* (2023.01); *H04N 23/611* (2023.01); *H04N 23/74* (2023.01); *H04N 23/90* (2023.01); *A61B 5/1126* (2013.01)

(58) Field of Classification Search
CPC .... H04N 23/957; H04N 23/56; H04N 23/611; H04N 23/74; H04N 23/90; A61B 5/1126
See application file for complete search history.

(56) References Cited

U.S. PATENT DOCUMENTS

2017/0085867 A1\* 3/2017 Baran .................... B41M 3/008

FOREIGN PATENT DOCUMENTS

| CN | 109854893 | 6/2019 |
|---|---|---|
| CN | 111343367 | 6/2020 |

(Continued)

OTHER PUBLICATIONS

CNIPA, First Office Action for CN Application No. 202310721980.3, Jul. 22, 2023.

*Primary Examiner* — Nasim N Nirjhar
(74) *Attorney, Agent, or Firm* — Hodgson Russ LLP

(57) ABSTRACT

A system for variable illumination intelligent imaging of a billion pixel light field includes a support, a light source, an acquisition array and a control system. The light source and the acquisition array are mounted on the support. The acquisition array includes whole body acquisition cameras configured to acquire whole images of a human body and detail acquisition cameras configured to acquire area detail images of the human body at a plurality of angles of view. The control system, respectively connected to the light source and the acquisition array, is configured to synchronously control the acquisition array, and control the light source and the acquisition array to synchronously acquire a current human body whole image and a current human body detail image of an acquired person after each illumination environment conversion based on a preset light source illumination mode and a conversion frequency.

5 Claims, 4 Drawing Sheets

(56) References Cited

FOREIGN PATENT DOCUMENTS

| CN | 111343367 | A | * | 6/2020 | ........... H04N 5/2251 |
|----|-----------|---|---|--------|-------------------------|
| CN | 213042291 |   |   | 4/2021 |                         |
| CN | 213042291 | U | * | 4/2021 |                         |
| CN | 112884822 | A | * | 6/2021 | ............... G06T 5/50 |

* cited by examiner

SYSTEM AND METHOD FOR VARIABLE ILLUMINATION INTELLIGENT IMAGING OF BILLION PIXEL LIGHT FIELD

CROSS-REFERENCE TO RELATED APPLICATIONS

This application claims priority to Chinese Patent Application No. 202310721980.3, filed on Jun. 19, 2023, the entire disclosure of which is incorporated by reference herein.

TECHNICAL FIELD

The disclosure relates imaging a field of light field intelligent imaging technologies, and particularly to a system and a method for variable illumination intelligent imaging of a billion pixel light field.

BACKGROUND

High quality human body digitization is a key technology in the fields of human body measurement, holographic communication, film and television production and virtual reality. More and more human body scanning service providers select a self-established system and a handheld device for human body acquisition. However, as requirements for accuracy of a human body model are improved, requirements for an acquired resolution and illumination are correspondingly improved.

For a 3D human body scanning cage, acquisition devices such as a scanner, a sensor or a digital single-lens reflex camera are mounted inside a stationary cage where a model stands on a central fixed or rotating platform to be captured from outside. For a handheld human body scanner, when a model remain as still as possible, various parts of a human body are scanned and captured by using a depth camera or an RGB camera, and sometimes, assistant positioning with a mark point or a structured light is needed.

The 3D human body scanning cage generally captures the whole human body in all directions. However, consideration cannot to be given to both the overall posture and the human body detail due to a limitation of an acquisition resolution. Meanwhile, the light source generally only uses simple LED lamps, and when the number of LED lamps is large, their control and synchronization are complex and expensive. The handheld human body scanner requires a long time to scan the whole human body, during which it is difficult to ensure that a scanned person does not move or change the posture, and an additional preparation time is required for using the mark point.

SUMMARY

A system for variable illumination intelligent imaging of a billion pixel light field is provided in a first aspect of embodiments of the disclosure. The system includes a support, a light source, an acquisition array and a control system, in which
  the light source and the acquisition array are mounted on the support;
  the acquisition array includes whole body acquisition cameras and detail acquisition cameras at a plurality of angles of view, in which the whole body acquisition cameras are configured to acquire whole images of a human body at the plurality of angles of view; and the detail acquisition cameras are configured to acquire area detail images of the human body at the plurality of angles of view; and
  the control system, respectively connected to the light source and the acquisition array, is configured to synchronously control the acquisition array, and control the light source and the acquisition array to synchronously acquire a current human body whole image and a current human body detail image of an acquired person after each illumination environment conversion based on a preset light source illumination mode and a conversion frequency.

A method for variable illumination intelligent imaging of a billion pixel light field is provided in a second aspect of embodiments of the present disclosure. The method includes:
  obtaining human body position information of an acquired person through a multi-view display by using cameras of an acquisition array in a non-trigger mode, wherein the cameras of an acquisition array comprise whole body acquisition cameras and detail acquisition cameras at a plurality of angles of view; the whole body acquisition cameras are configured to acquire whole images of a human body at the plurality of angles of view; and the detail acquisition cameras are configured to acquire area detail images of the human body at the plurality of angles of view;
  obtaining a plurality of groups of illumination environment information by controlling a light source to switch the light source at a preset switching frequency in response to a switching instruction; and
  obtaining current human body whole images and current human body detail images at the plurality of angles of view based on the human body position information by performing a variable illumination acquisition based on a preset acquisition mode and the plurality of groups of illumination environment information.

Additional aspects and advantages of the present disclosure will be set forth in part in the following description, and in part will become obvious from the following description, or may be learned by practice of the disclosure.

BRIEF DESCRIPTION OF THE DRAWINGS

The above and/or additional aspects and advantages of the present disclosure will become obvious and easy to understand from the following description of the embodiments in conjunction with the accompanying drawings.

DETAILED DESCRIPTION

Embodiments of the present disclosure are described in detail below, and examples of embodiments are illustrated in the accompanying drawings, in which the same or similar labels represent the same or similar elements or elements with the same or similar functions. The embodiments described below with reference to the drawings are exemplary, is intended to be configured to explain the present disclosure and are not to be construed as a limitation of the present disclosure.

A system, a method and an apparatus for variable illumination intelligent imaging of a billion pixel light field proposed in embodiments of the present disclosure are described referring to attached drawings.

A system for variable illumination intelligent imaging of a billion pixel light field provided in embodiments of the present disclosure is described referring to attached drawings.

Figure 1:
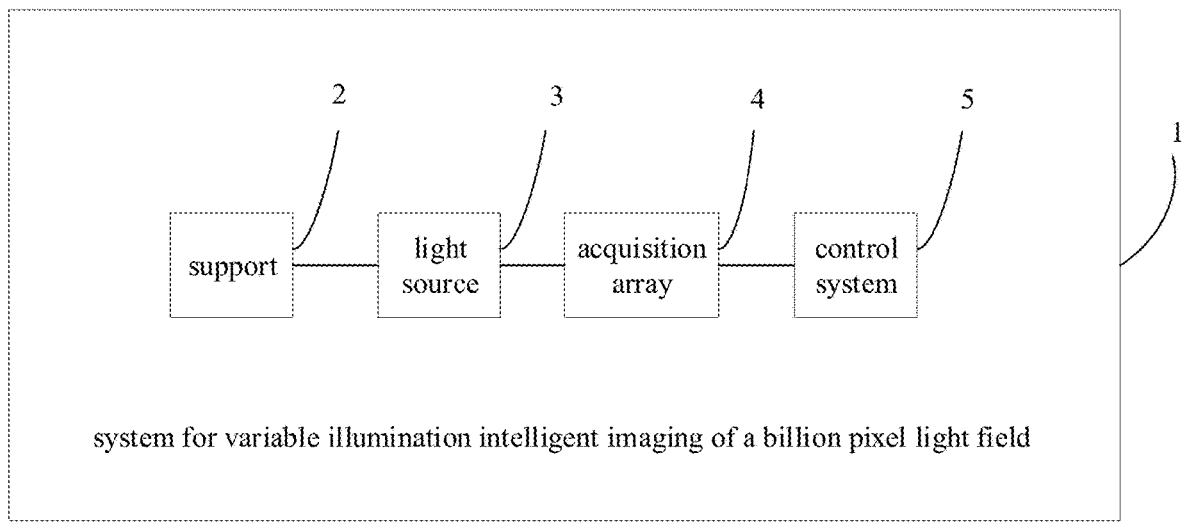
FIG. 1 is a diagram illustrating a structure of a system for variable illumination intelligent imaging of a billion pixel light field according to embodiments of the present disclosure.

FIG. 1 is a diagram illustrating a structure of a system 1 for variable illumination intelligent imaging of a billion pixel light field according to embodiments of one the present disclosure.

As illustrated in FIG. 1, the system 1 for variable illumination intelligent imaging of a billion pixel light field includes a support 2, a light source 3, an acquisition array 4 and a control system 5.

The light source 3 and the acquisition array 4 are mounted on the support 2.

The acquisition array 4 includes whole body acquisition cameras and detail acquisition cameras at a plurality of angles of view. The whole body acquisition cameras are configured to acquire whole images of a human body at the plurality of angles of view. The detail acquisition cameras are configured to acquire area detail images of the human body at the plurality of angles of view.

The control system 5, respectively connected to the light source 3 and the acquisition array 4, is configured to synchronously control the acquisition array 4, and control the light source 3 and the acquisition array 4 to synchronously acquire a current human body whole image and a current human body detail image of an acquired person after each illumination environment conversion based on a preset light source illumination mode and a conversion frequency.

It may be understood that, the whole body acquisition camera is configured to capture a whole image of a human body at the angle of view. The detail acquisition camera is configured to capture area detail images of the human body at the angle of view. Further, a high brightness LED screen mounted on the support and pointing to the human body may be configured to provide an illumination environment of wide range and multi-angle, and dynamically modify a screen display content, which may achieve high frequency switching of the illumination environment. The control system connected to the light source and the acquisition array, first plays an acquisition array synchronization function, then may preconfigure an illumination mode and a conversion frequency, and may synchronously acquire a current whole body image and detail image after each illumination environment conversion by jointly controlling the light source and the acquisition array.

Figure 2:
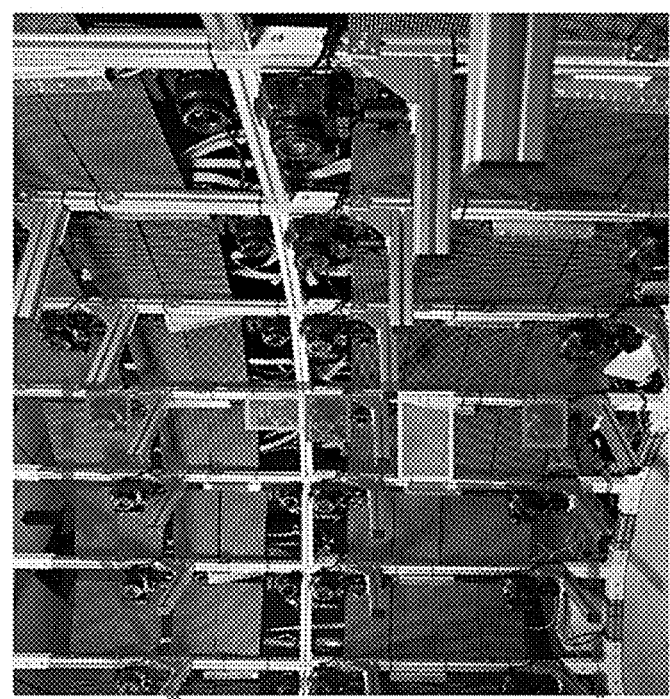
FIG. 2 is a diagram illustrating mounting of a support according to embodiments of the present disclosure.
Figure 2:
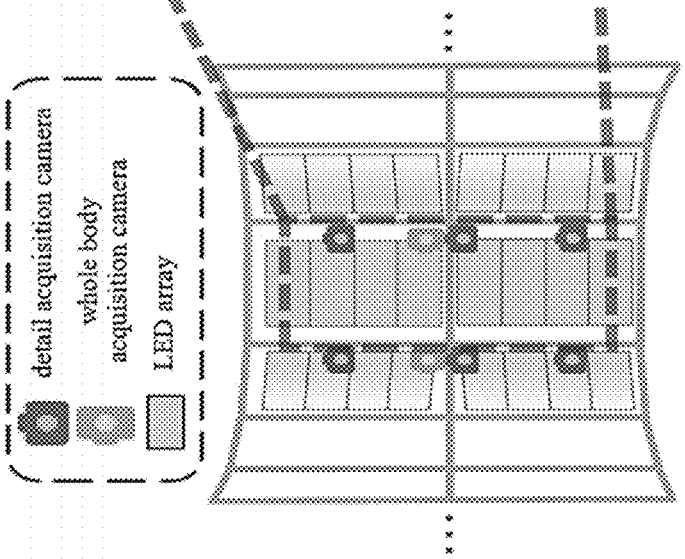
Figure 2:
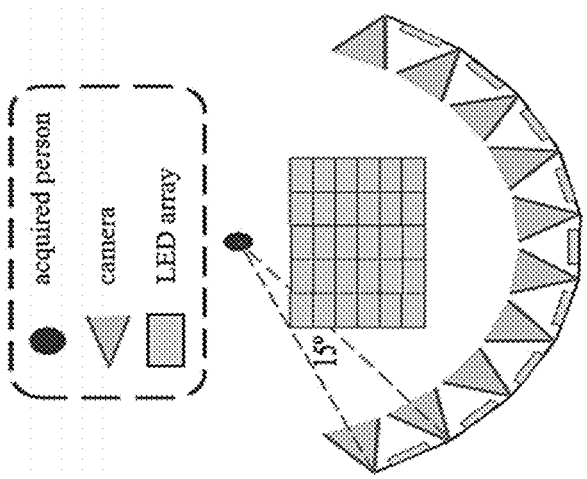

In an embodiment, as illustrated in FIG. 2, (a) in FIG. 2 is a top view; (b) in FIG. 2 is a front view; and (c) in FIG. 2 is a physical object view. The support 2 is a semicircular cage structure with a height of 2.3 m and a radius of 2 m, and the acquired person stands at the center of the support behind which is a replaceable curtain. The acquisition array is divided into ten groups and points to the center, each of which includes a whole body acquisition camera and three detail acquisition cameras, and a central angle for two adjacent groups is 15°, that is, a total of 135° angle of view directly in front of the human body can be covered. The whole body acquisition camera is mounted at an arc of the support, the height may be dynamically adjusted, and may be placed at the height of 1 m for a default human body; the detail acquisition camera is fixed at the arc through a horizontal rod horizontally pointing to the center, and a camera posture, a camera height and a distance between a camera and the center may be dynamically adjusted by adjusting the height of the horizontal rod and the position of the camera on the horizontal rod. Three detail acquisition cameras at the same angle of view may be respectively placed at heights of 1.75 m, 1.05 m and 0.35 m, to respectively acquire details of areas such as a face, a body center and a lower limb.

In an embodiment of the disclosure, the whole body acquisition camera and the detail acquisition camera are configured to acquire an original color image and perform a human body task detection and a human body detail texture analysis respectively, to achieve ultra-high precision reconstruction of the human body.

Specifically, a 1500 D single-lens reflex camera is selected as the whole body acquisition camera to acquire 6000*4000 original color images, which may support tasks such as human body positioning, posture detection and synchronous registration, and an R5 single-lens reflex camera is selected as the detail acquisition camera to acquire 8191*5463 resolution original color images, which may support an analysis on texture details such as a human face, skin and clothing materials, to achieve ultra-high-precision human body reconstruction.

In an embodiment of the present disclosure, the light source 3 includes a plurality of light emitting devices, and the light emitting devices are LED arrays, each LED array is 320*160 mm in size and includes 64*32 LED pixels. The LED arrays are mounted on the cambered surface and the top of the support by a connector, and 8 LED arrays are mounted from top to bottom on the cambered surface of the support between two adjacent groups of acquisition cameras, namely, 8 rows and 9 columns of LED arrays are distributed on the cambered surface. Thus, light rays at a plurality of angles may be provided to illuminate the acquired person, which avoids that a light dead angle appears within the view angle of the acquisition array, thereby affecting a capture effect. 6 rows and 5 columns of closely arranged LED arrays are mounted on the top of the support, which may provide a large-area light ray illuminating from the upper side. Each LED array is connected to a LED screen receiving card, intelligent centralized control of all LED arrays is achieved by a software and a controller, and indoor and outdoor complex illumination environments can be simulated and an illumination mode switching frequency can be set.

Figure 3:
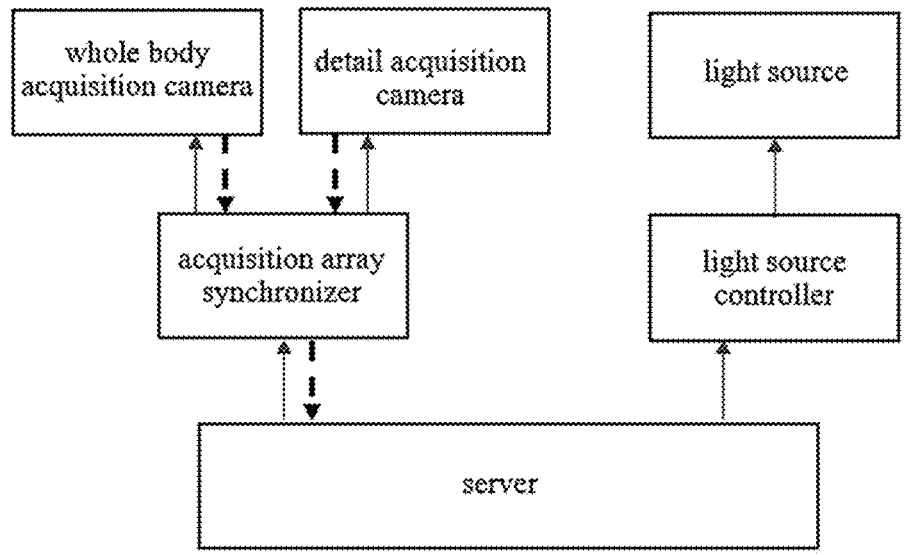
FIG. 3 is a diagram illustrating a structure of a control system according to embodiments of the present disclosure.

In an embodiment of the disclosure, as illustrated in FIG. 3, the control system 5 includes a server, a light source controller and an acquisition array synchronizer, and the server can synchronously control the acquisition array and the light source via a software, and automatically gathers human body images after each acquisition is completed through a USB acquisition card.

The system for variable illumination intelligent imaging of a billion pixel light field according to embodiments of the present disclosure, can achieve multi-angle synchronous acquisition of whole human body images and human body detail images in a short time by jointly controlling a system of acquisition and illumination, and a total resolution at each acquisition can be up to a billion pixel level, which provides rich variable illumination images for technologies such as human body reconstruction and new angle of view generation, and has a high precision of system data, rich support modes and a high acquisition efficiency.

Second, a method for variable illumination intelligent imaging of a billion pixel light field provided in embodiments of the present disclosure is described referring to attached drawings.

Figure 4:
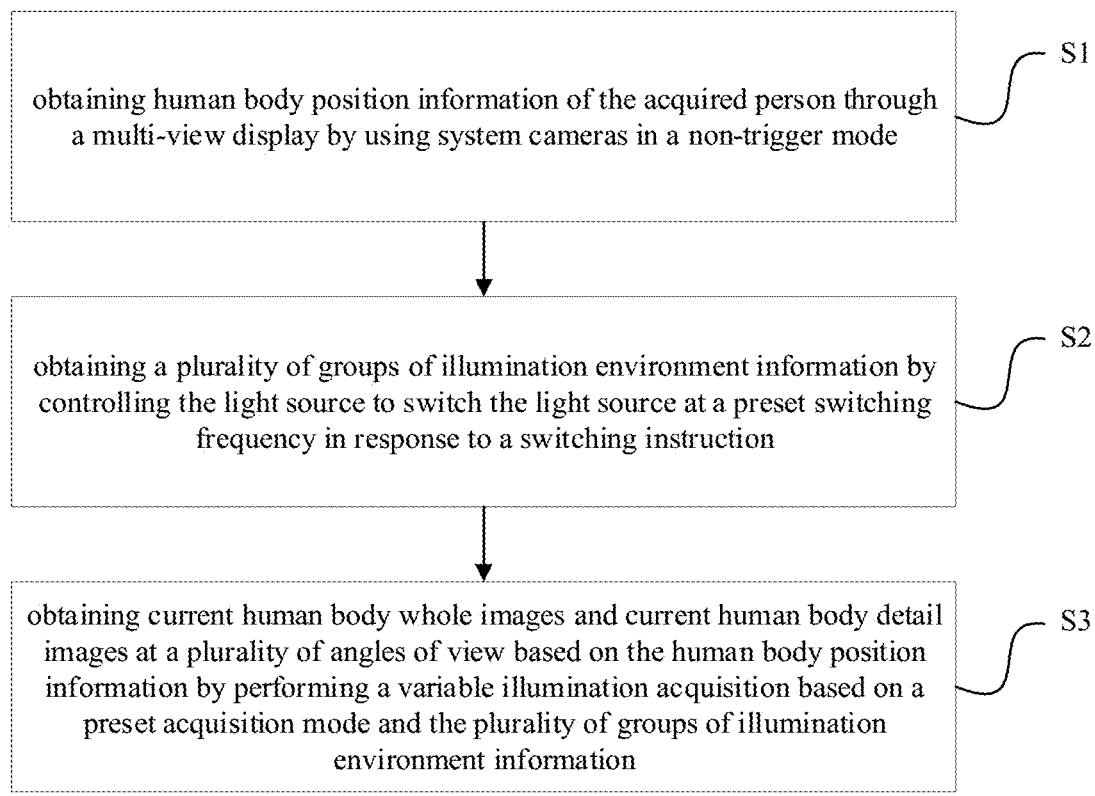
FIG. 4 is a flowchart illustrating a method for variable illumination intelligent imaging of a billion pixel light field according to embodiments of the present disclosure.

FIG. 4 is a flowchart illustrating a method for variable illumination intelligent imaging of a billion pixel light field according to embodiments of the present disclosure.

As illustrated in FIG. 4, the method includes the following steps.

At block S1, human body position information of the acquired person is obtained through a multi-view display by using system cameras in a non-trigger mode.

At block S2, a plurality of groups of illumination environment information are obtained by controlling the light source to switch the light source at a preset switching frequency in response to a switching instruction.

At block S3, current human body whole images and current human body detail images at a plurality of angles of view are obtained based on human body position information by performing a variable illumination acquisition based on a preset acquisition mode and the plurality of groups of illumination environment information.

Specifically, the method may include the following steps.

At step 1, an acquired person enters an acquisition system, cameras are set in a non-trigger mode, a multi-view display is turned on, and it is observed whether the position of the human body is proper and an adjustment is made.

At step 2, the light source is controlled, a plurality of groups of simulated illumination environments are circularly switched and displayed. Taking 10 groups of illumination environments for example, it may be set to switch to a next illumination environment every 0.3 s, to complete one round of circulation in 3 s.

At step 3, the acquisition array is set in a synchronous continuous capture mode, a trigger interval is set to be consistent with an illumination environment switching frequency for variable illumination acquisition. The control software collects whole body and detail images at 10 angles of view simultaneously by a synchronous box. The images are stored in the memory first, when 10 groups of illumination environments are acquired, the control software sets the camera to stop acquisition, and the images are gathered to a hard disk of a server.

At step 4, the acquired person leaves the acquisition system, and a next round of acquisition starts.

The method for variable illumination intelligent imaging of a billion pixel light field according to embodiments of the present disclosure, can achieve multi-angle synchronous acquisition of a whole human body and human body detail in a short time by jointly controlling a system of acquisition and illumination, and a total resolution at each acquisition can be up to a billion pixel level, which provides rich variable illumination images for technologies such as human body reconstruction and new angle of view generation, and has a high precision of system data, rich support modes and a high acquisition efficiency.

Figure 5:
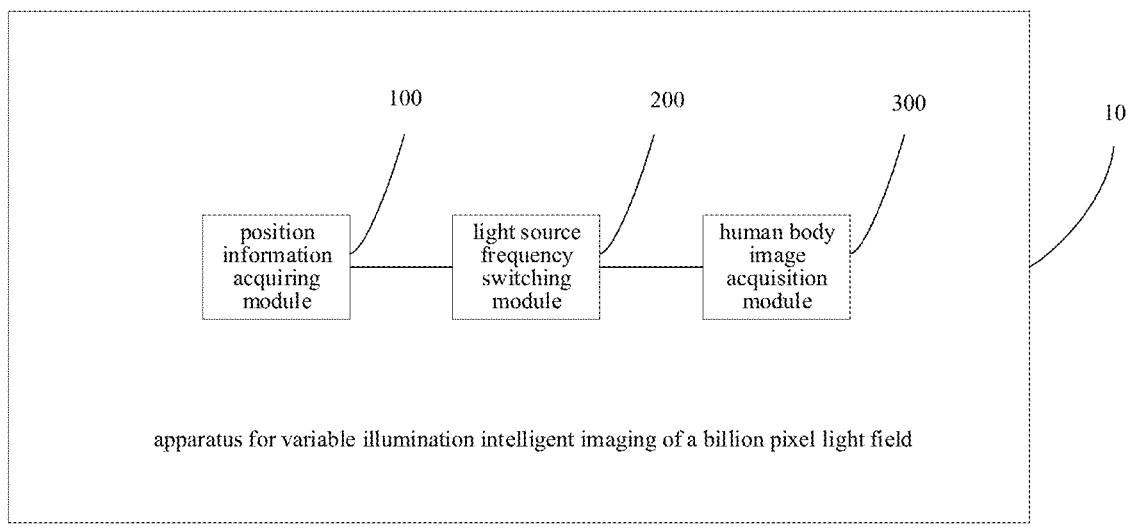
FIG. 5 is a diagram illustrating a structure of an apparatus for variable illumination intelligent imaging of a billion pixel light field according to embodiments of the present disclosure.

To achieve the above embodiments, as illustrated in FIG. 5, an apparatus 10 for variable illumination intelligent imaging of a billion pixel light field is further provided in the embodiment. The apparatus includes a position information acquiring module 100, a light source frequency switching module 200 and a human body image acquisition module 300.

The position information acquiring module 100 is configured to obtain human body position information of an acquired person through a multi-view display by using system cameras in a non-trigger mode.

The light source frequency switching module 200 is configured to obtain a plurality of groups of illumination environment information by controlling a light source to switch the light source at a preset switching frequency in response to a received switching instruction.

The human body image acquisition module 300 is configured to obtain current human body whole images and current human body detail images at a plurality of angles of view based on the human body position information by performing a variable illumination acquisition based on a preset acquisition mode and the plurality of groups of illumination environment information.

Further, the preset acquisition mode includes a synchronous continuous capture mode in which a trigger interval of an acquisition array is adjusted to the preset switching frequency.

The apparatus for variable illumination intelligent imaging of a billion pixel light field according to embodiments of the present disclosure, can achieve multi-angle synchronous acquisition of a whole human body and human body detail in a short time by jointly controlling a system of acquisition and illumination, and a total resolution at each acquisition can be up to a billion pixel level, which provides rich variable illumination images for technologies such as human body reconstruction and new angle of view generation, and has a high precision of system data, rich support modes and a high acquisition efficiency.

In addition, terms "first" and "second" used in the present disclosure are only for description purpose, and may not be understood as indicating or implying a relative importance or implying a number of technical features indicated by implication. Therefore, features limiting "first" and "second" may explicitly or implicitly include at least one of the features. In the description of the disclosure, "a plurality of" means at least two, for example two, three, etc., unless otherwise specified.

In descriptions of the specification, descriptions with reference to terms "one embodiment", "some embodiments", "example", "specific example" or "some examples" etc. mean specific features, structures, materials or characteristics described in conjunction with the embodiment or example are included in at least one embodiment or example of the present disclosure. In this specification, the schematic representations of the above terms do not have to be the same embodiment or example. Moreover, specific features, structures, materials or characteristics described may be combined in any one or more embodiments or examples in a suitable manner. In addition, those skilled in the art may combine different embodiments or examples and characteristics of different embodiments or examples described in this specification without contradicting each other.

It should be understood that, notwithstanding the embodiments of the present disclosure are shown and described above, the above embodiments are exemplary in nature and shall not be construed as a limitation of the present disclosure. Those skilled in the art may change, modify, substitute and vary the above embodiments within the scope of the disclosure.

What is claimed is:

1. A system for variable illumination intelligent imaging of a billion pixel light field, comprising a support, a light source, an acquisition array, a control system, and a high brightness LED screen, wherein:

the light source and the acquisition array are mounted on the support;

the acquisition array comprises whole body acquisition cameras and detail acquisition cameras at a plurality of angles of view, wherein the whole body acquisition cameras are configured to acquire whole images of a human body at the plurality of angles of view, and the detail acquisition cameras are configured to acquire area detail images of the human body at the plurality of angles of view;

the control system, respectively connected to the light source and the acquisition array, is configured to synchronously control the acquisition array, and control the light source and the acquisition array to synchronously acquire a current human body whole image and a current human body detail image of an acquired person after each illumination environment conversion based on a preset light source illumination mode and a conversion frequency;

the high brightness LED screen is mounted on the support and points to the human body, and is configured to provide an illumination environment of wide range and multi-angle and dynamically update a screen display content to achieve high frequency switching of the illumination environment;

the support is a semicircular cage structure, and the acquired person is at a center position of the cage structure;

the acquisition array is divided into a plurality of groups and points to the center position, wherein each group of the acquisition array comprises a whole body acquisition camera and three detail acquisition cameras;

the whole body acquisition camera is mounted at an arc position of the cage structure, and the detail acquisition cameras are mounted at the arc position by a horizontal rod horizontally pointing to the center position, to dynamically adjust a camera posture, a camera height and a distance between a camera and the center by adjusting a height of the horizontal rod and a position of the camera on the horizontal rod; and the whole body acquisition camera and the detail acquisition cameras are configured to acquire an original color image and perform a human body task detection and a human body detail texture analysis respectively, to achieve ultra-high precision reconstruction of the human body.

2. The system according to claim 1, wherein the light source comprises a plurality of light emitting devices.

3. The system according to claim 2, wherein the control system comprises a server, a light source controller, and an acquisition array synchronizer, and the server is configured to synchronously control the acquisition array and the plurality of light emitting devices via the acquisition array synchronizer and the light source controller.

4. A method for variable illumination intelligent imaging of a billion pixel light field, comprising:

obtaining human body position information of an acquired person through a multi-view display by using cameras of an acquisition array in a non-trigger mode mounted on a support, wherein the cameras of the acquisition array comprise whole body acquisition cameras and detail acquisition cameras at a plurality of angles of view, the whole body acquisition cameras are configured to acquire whole images of a human body at the plurality of angles of view, and the detail acquisition cameras are configured to acquire area detail images of the human body at the plurality of angles of view; wherein the support is a semicircular cage structure, and the acquired person is at a center position of the cage structure; the acquisition array is divided into a plurality of groups and points to the center position, wherein each group of the acquisition array comprises a whole body acquisition camera and three detail acquisition cameras; the whole body acquisition camera is mounted at an arc position of the cage structure, and the detail acquisition cameras are mounted at the arc position by a horizontal rod horizontally pointing to the center position, to dynamically adjust a camera posture, a camera height and a distance between a camera and the center by adjusting a height of the horizontal rod and a position of the camera on the horizontal rod; the whole body acquisition camera and the detail acquisition cameras are configured to acquire an original color image and perform a human body task detection and a human body detail texture analysis respectively, to achieve ultra-high precision reconstruction of the human body;

obtaining a plurality of groups of illumination environment information by controlling a light source mounted on the support to switch the light source at a preset switching frequency in response to a switching instruction, wherein a high brightness LED screen mounted on the support and pointing to the human body provides an illumination environment of wide range and multi-angle and dynamically updates a screen display content to achieve high frequency switching of the illumination environment; and obtaining current human body whole images and current human body detail images at the plurality of angles of view based on the human body position information by performing a variable illumination acquisition based on a preset acquisition mode and the plurality of groups of illumination environment information.

5. The method according to claim 4, wherein the preset acquisition mode comprises a synchronous continuous capture mode, wherein a trigger interval of the acquisition array is adjusted to the preset switching frequency.

* * * * *